United States Patent [19]
van den Burg

[11] Patent Number: 5,143,695
[45] Date of Patent: Sep. 1, 1992

[54] PROCESS AND DEVICE FOR THE CONTINUOUS ANALYSIS OF THE COMPOSITION OF GASES

[75] Inventor: Johannes M. E. van den Burg, Houten, Netherlands

[73] Assignee: Mijnhardt B.V., Bunnik, Netherlands

[21] Appl. No.: 790,143

[22] Filed: Nov. 7, 1991

Related U.S. Application Data

[63] Continuation of Ser. No. 500,738, Mar. 28, 1990.

[30] Foreign Application Priority Data

Mar. 31, 1989 [NL] Netherlands ............... 8900800

[51] Int. Cl.$^5$ .............................. A61B 5/08
[52] U.S. Cl. ..................... 422/84; 436/900; 128/716; 128/719; 128/725; 73/23.3
[58] Field of Search .......... 422/84; 128/716, 719, 128/725, 707; 436/900; 73/23.3

[56] References Cited

U.S. PATENT DOCUMENTS

| | | | |
|---|---|---|---|
| 3,903,742 | 9/1975 | Colton | 128/725 |
| 4,094,187 | 6/1978 | Navarre | 73/1 G |
| 4,237,904 | 12/1980 | Franetzki | 128/725 |
| 4,274,425 | 6/1981 | Lutz et al. | 422/84 |
| 4,278,636 | 7/1981 | Voigt et al. | 422/84 |
| 4,298,010 | 11/1981 | Eckstein et al. | 128/719 |
| 4,316,380 | 2/1982 | Heim et al. | 73/23.3 |
| 4,316,382 | 2/1982 | Woodruff | 73/23.2 |
| 4,448,058 | 5/1984 | Jaffe et al. | 128/719 |
| 4,850,371 | 7/1989 | Broadhurst et al. | 128/719 |
| 4,884,460 | 12/1989 | Nowacki et al. | 128/725 |
| 4,900,514 | 2/1990 | Fuller | 422/84 |

Primary Examiner—Robert J. Warden
Assistant Examiner—Theresa A. Trembley
Attorney, Agent, or Firm—Michael N. Meller

[57] ABSTRACT

Process for the continuous analysis of the composition of gases, by means of a measuring head for determining the flow rate and analysis equipment which is placed a distance away from the measuring head and is connected thereto by a sample line, a calibration gas being fed to the sample line at the measuring head, by means of which the transit time of the gases is determined, and by means of this transit time a phase shift is introduced during the determination of the connection between the flow rate and the composition. According to the invention a series of calibration gas impulses are fed from the equipment, and the average transit time of the gases in the conditions prevailing locally at that moment is determined therewith, for the essentially continuous determination of the connection between the flow rate and the composition.

Device for carrying out the process comprising a measuring head and analysis equipment for determining the composition of the gases, provided with a source of calibration gas in the analysis equipment, a calibration gas line connected to the sample line a short distance from the suction aperture thereof with the measuring head, means for maintaining the calibration gas under pressure, and means for periodically opening a valve in the calibration gas line, and means for determining the transit time of the calibration gas impulses through the sample line.

9 Claims, 2 Drawing Sheets

PROCESS AND DEVICE FOR THE CONTINUOUS ANALYSIS OF THE COMPOSITION OF GASES

This application is a continuation of application Ser. No. 500,738, filed Mar. 28, 1990.

BACKGROUND OF THE INVENTION

The invention relates to a process for the continuous analysis of the composition of gases, by means of a measuring head which is used for determining the flow rate of the gases to be measured as a function of time, while the composition is analyzed using analysis equipment which is placed a distance away from the measuring head and is connected thereto by a sample line through which gas is drawn using a suction pump.

If one wishes to analyze the composition of gases in a way when such composition does not change much over time, or if one is interested only in the average composition, position can fluctuate greatly and one wishes to follow that fluctuation with great accuracy, and particularly where one also wishes to find a correlation with the flow rate of the gases to be measured, a problem is caused by the fact that the measurement of the flow rate takes place immediately, whereas and the measurement of the concentrations is delayed in time due to the distance of the analysis equipment from the measuring head. In order to correct this time difference, the procedure hitherto has been to feed in by hand, using a balloon, a quantity of a suitable calibration gas in or near the suction aperture of the sample line at the measuring head, and then to determine from the observed time of entry of said calibration gas into the analysis equipment the time required for the flow the gas through the sample line from the measuring head to the analysis equipment. This time will hereinafter be referred to as the "transit time". This calibration is, however, not accurate, on the one hand because the time of delivery of a quantity of calibration gas by hand cannot be determined accurately, or cannot be correlated accurately with the reading in the analysis equipment and, on the other hand, because the transit time is not a constant. In fact, said transit time depends on all kinds of environmental conditions, the temperature being the main factor, but the atmospheric pressure and, for example, the moisture content of the gas to be analyzed also playing a role. Carrying out measurements on gases with variations in the composition with a period of 2 to 3 seconds was therefore so inaccurate that it can be said that such measurements were hitherto impossible.

THE OBJECTS OF THE INVENTION

The object of the present invention is to provide a solution to this problem and thus to propose a process as well as a device capable of continuously measuring accurately the composition of gases containing variations in the composition which occur during a period of a few seconds.

SUMMARY OF THE INVENTION

To this end, in the process according to the invention a series of calibration gas impulses are fed from the equipment, and the average transit time of the gases in the conditions prevailing locally at that moment is determined therewith, in order to be able to substantially continuously correlate the flow rate and the composition of the gas.

Controlling the delivery of calibration gas impulses from the equipment in this way permits a greater accuracy in the determination of the time at which each pulse is recorded by the equipment again. Any noise phenomena found are overcome by taking an average over a series of calibration gas impulses. The averaging of a series of measurements is thus carried out for the purpose of increasing calibration accuracy and, of course, not for the purpose of removing the effect of possibly changing circumstances. On the contrary, with the idea of the invention it is very easily possible to carry out renewed calibration with great frequency, once it is suspected that a change in circumstances has occurred, or to ensure that such a change has not occurred.

The choice of a calibration gas will be determined by the analysis facilities in the equipment. If said equipment is, for example, suitable for analyzing the carbon dioxide content, carbon dioxide can by used as the calibration gas.

The invention also relates to a device for carrying out the process described above, which device comprises a measuring head which can be connected to the source of the gases to be analyzed, said measuring head being provided with a volume transducer or similar instrument for the continuous determination of the flow rate of the gases to be measured as a function of time, and analysis equipment for determining the composition of the gases, provided with a suction pump is coupled to which in turn connects a sample line connecting the measuring head to the analyzer is connected.

According to the invention, said device is characterized by a source of calibration gas in the analysis equipment, a calibration gas line connected line to the sample line at a place a short distance from the suction aperture of the sample line at with the measuring head, means for placing or maintaining the source of calibration gas under pressure, and means for opening a valve in the calibration gas line periodically for the injection of calibration gas impulses, and means for determining the transit time of said calibration gas impulses through the sample line.

The moisture content of the gas to be analyzed can have a relatively great influence on the transit time. This applies in particular when, as is often the case, the gas to be analyzed is virtually saturated with water vapor. Cooling down, and thus condensation, occurs in the sample hose. This alters the resistance of the sample line, and thereby also the transit time from the sampling point to the analyzer.

In order to overcome this problem, the device according to the invention is preferably designed in such a way that the sample line is made of a material which is permeable to water vapor over at least part of the length.

If this part of the sample line is long enough, the relative humidity can be made to fall below the condensation threshold, so that the above-mentioned alterations in the transit time are prevented.

A major field of application of the invention is the analysis of human respiration air, in particular for the examination of metabolism processes. The measuring head is then a pipe section through which the person to be examined breathes in and out, and the analysis equipment is designed for determining the $O_2$ and $CO_2$ concentrations. With the invention it is possible to establish accurately between each inspiration and expiration the connection between the concentration of those two gases and the volume breathed in and out.

DETAILED DESCRIPTION OF THE INVENTION

Figure 1:
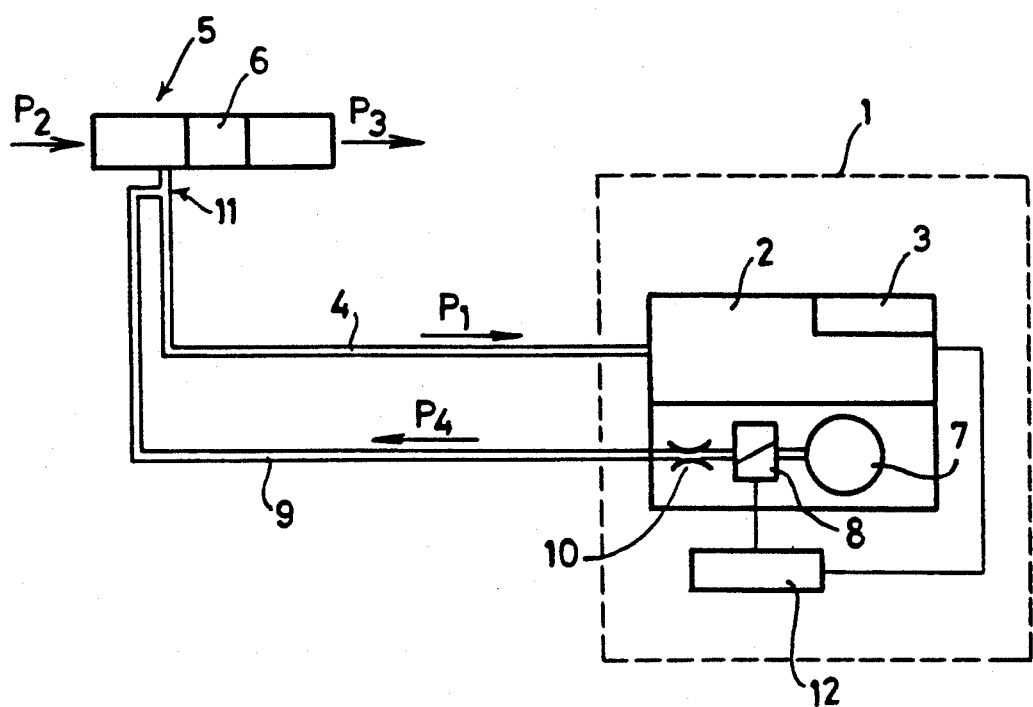
FIG. 1 shows a diagram of the device.

The analysis equipment 1 comprises the gas analyzer proper which is indicated by 2, and which is provided with a suction pump 3. The latter constantly draws gas through the sample line 4, as indicated by the arrow Pl, from the measuring head, indicated in its entirety by 5. The gases to be analyzed enter said measuring head in the direction of the arrow P2, and leave the head in the direction of the arrow P3. The flow passage of the measuring head contains an instrument 6 such as a volume transducer for determining the flow rate of the gas passing therethrough.

The analysis equipment also contains a tank 7 for a calibration gas under pressure. It can be delivered by a valve 8 to a calibration gas line 9 with a flow resistor 10 for accurately determining the quantity of calibration gas flowing therethrough being interposed between valve 8 and line 9. This calibration gas flows in the direction of the arrow P4. The calibration gas line is connected to said sample line 4 at a juncture indicated by 11 close to the suction aperture of the sample line 4 at the measuring head.

Under the control of an electronic control unit, indicated in its entirety by 12, the valve 8 can be opened and closed periodically, in order thus to deliver calibration gas pulses which enter the sample line at juncture 11 and then reach the analyzer 2. The time of arrival of each calibration gas pulse at the analyzer is then fed back to the electronic unit 12, so that the transit time from the point 11 to the entrance of the analyzer can be established.

It is possible, for example, to work with series of ten calibration gas impulses, each with a duration of 1 second, and with intervals between impulses of 1 second. The first and second pulses are then used only for flushing the line 9 with the calibration gas, and the pulses 3 to 10 are used for the measurement.

Figure 2:
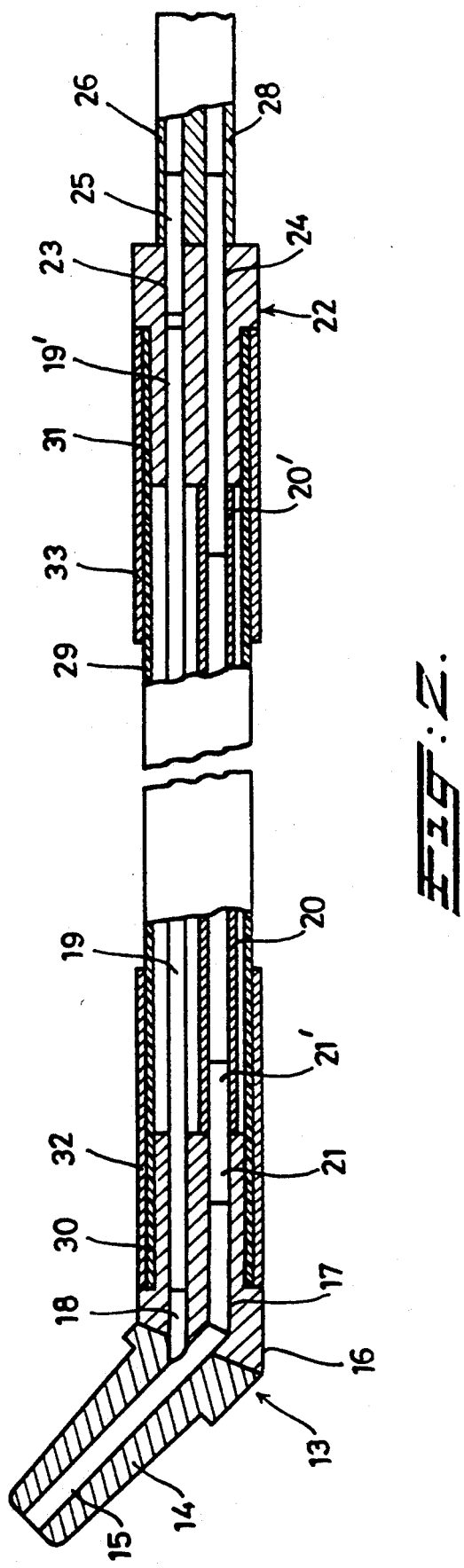
FIG. 2 shows an embodiment, partially in longitudinal section, of a double connecting hose between the measuring head and the analysis equipment.

FIG. 2 shows an advantageous embodiment of a combination of the sample line 4 and the calibration gas line 9. The connecting piece 13 is made kinked, so that the bores to be described below can be made easily. The part 14 tapers slightly on the outside, so that it can be inserted easily in a suitable aperture into the measuring head. It is provided with an axial bore 15.

The other part 16 in the embodiment shown in FIG. 2 is at an angle of approximately 135° relative to the part 14. It is provided with two longitudinal bores 17, 18. It appears from the drawing that as a result of the angle between the parts 14 and 16, both bores 17 and 18 can connect to bore 15.

A flexible thin tube 19 is inserted over some distance into bore 18 and can, for example, be glued in it It is made of a material which is permeable to water vapor and serves as a stabilization hose. Another flexible tube is inserted into the bore 17, not directly in the same way as tube 19, but a short pipe section 21, which can be, for example, of metal, is inserted into bore 17 and also projects over some distance beyond the connecting piece, as shown by 21', so that it can be used for sliding on and possibly gluing the tube material 20. The latter serves as a calibration gas line.

The tubes 19 and 20 are fixed in a similar way to the coupling piece 22, which again has two parallel longitudinal bores 23, 24. The end of the flexible tube 19, indicated by 19', is slid over some distance into bore 23. At the other side a short metal pipe 25 is again inserted into the bore; the flexible tube 26 is slid onto the part of pipe 25 projecting beyond the coupling piece.

The bore 24 in the coupling piece, has a metal pipe 27 which projects beyond the coupling piece 22 at both sides. The end of the tube 20' is slid onto the projecting end at one side. At the other side the flexible tube 28 is slid onto metal pipe 27.

The tube sections 19 and 20 between the connecting piece 13 and the coupling piece 22 are surrounded by a common sleeve 29, which is slid at one side onto the connecting piece 13 at a part 30 with reduced diameter, and at the other side onto a part 31 with reduced diameter of the coupling piece 22. The sleeve 29 serves to keep the tubes 19 and 20 together, but it must, of course, be made of an openwork material such as a woven material, in order to enable tube 20 to fulfill its function. Finally, short muffs 32, 33 are respectively slid over the connecting points on the connecting piece 13 and coupling piece 22, as a stabilization of the connections between the tubes 19 and 20 and the pieces 13 and 22.

The length of the tube sections 19 and 20 between the connecting piece 13 and the coupling piece 22 is determined by the length needed to reduce the moisture content of the sample gas below the condensation threshold by means of the tube 19 which is permeable to water vapor. The tubes 26 and 28 then bridge the remainder of the distance between the measuring head and the analysis equipment. These tubes 26 and 28 can also be connected to each other over the entire length, so that in cross-section the shape of an 8 is produced, which is the embodiment shown in FIG. 2.

In order to give a good understanding of the effect achieved with the invention, it can be said that in a specific application a sample line 4 between the measuring head and the analysis equipment 1 is approximately 1.8 m long. The suction pump draws 200 to 250 ml per minute of gas through, said sample line out of the measuring head 5 for analysis. The transit time will then be approximately 1 second. In a composition that fluctuates with periods of 2 to 3 seconds, in order to be able to establish a correlation continuously between the gas composition and the flow rate, the transit time of the sample gas through the sample line must be known with an accuracy of less than 5 msec. This can be achieved in principle if a series of ten impulses of the calibration gas is sent out, in such a way that the valve is alternatingly opened 1 second and closed 1 second. This injection of sample gas can take place at a flow rate of 100 to 150 ml per minute. As already noted, when the sample line 4 is 1.8 m long, the transit time is approximately 1.0 sec. Without moisture stabilization the transit time could vary up to 100 msec as a result of condensation, this being approximately 10% of the value of the transit time. In the specific embodiment mentioned, approximately 40 cm was found to be long enough for the moisture stabilization hose 19 to maintain a constant transit time not affected by moisture.

Finally, it is pointed out that in applying the invention in a device for analyzing human respiration air, the measuring head 5 is the so-called patient mouthpiece with built-in volume transducer. Unlike the analysis of, for example, flue gases, which always run in the same direction according to the arrows P2 and P3 shown in FIG. 1, the air flows through the patient mouthpiece in two directions; the arrows P2 and P3 indicate the direction of flow during inhalation but that direction of flow is reversed for the inspiration.

What is claimed is:

1. A process for continuously determining the correlation between the flow rate and the composition of gases which may fluctuate greatly and which pass through a measuring head which determines the flow rate of said gases comprising:
providing a measuring head which determines the flow rate of gases, whose composition may fluctuate greatly; analyzing
the composition of said gases being analyzed using analysis equipment which is placed a distance away from the measuring head and is connected thereto by a sampling line through which it is drawn using a suction pump; providing a calibration gas for determining transit time between the measuring head and the analysis equipment being fed via a calibration gas line to the sampling line at a point near where the sampling line connects to the measuring head, said calibration gas being fed as a series of calibration gas impulses from the analyzing equipment to the sampling line via the calibration gas line; and determining the average transit time of the gases in the conditions prevailing locally at the moment using said analyzing equipment for substantially continuously determining the correlation between the flow rate and the gas composition.

2. A device for accurately correlating flow rate measurement data and gas composition data for a flowing gas having composition which may fluctuate greatly comprising:
a measuring head through which flowing gas having a composition which may fluctuate greatly passes to be analyzed, said measuring head being provided with a volume transducer; means for continuously determining the flow rate of the flowing gas flowing through said measuring head; analysis means for determining the composition of said flowing gas; a sampling line connecting said measuring head to said analysis means; suction means for drawing said gas flowing through the measuring head to the analysis means via the sampling line; a source of pressurized calibration gas for determining the transit time between said measuring head and said analysis means; a calibration gas line for coupling said source of pressurized calibration gas to said sampling line at a juncture located near the end of said sampling line which is connected to said measuring head; a valve located in said analysis means between said source of pressurized calibration gas and said calibration gas line, said valve being operable between an open and a closed position; means for periodically opening and closing said valve at a predetermining rate to inject pressurized calibration gas impulses into said sampling line at said predetermined rate; and means for determining the transit time of said pressurized calibration gas impulses through said sampling line.

3. A device in claim 2, further comprising a connecting piece having first bore means which communicate with an aperture of said measuring head, said first bore means forming part of said sampling line, and having second bore means which communicate with said first bore means at a point intermediate the ends of said first bore means, said second bore means forming part of said gas calibration line.

4. A device according to claim 3 for analysis of human respiration air, wherein the measuring head is a mouthpiece with a built-in volume transducer, said mouthpiece capable of allowing airflow in two directions, for the inspiration and expiration of air.

5. A device as in claim 3, wherein said connecting piece and said first bore means are kinked.

6. A device according to claim 5 for analysis of human respiration air, wherein the measuring head is a mouthpiece with a built-in volume transducer, said mouthpiece capable of allowing airflow in two directions, for the inspiration and expiration of air.

7. A device as in claim 2, wherein said sampling line is made along at least part of its length of material which is permeable to water vapor.

8. A device according to claim 7 for analysis of human respiration air, wherein the measuring head is a mouthpiece with a built-in volume transducer, said mouthpiece capable of allowing airflow in two directions, for the inspiration and expiration of air.

9. A device according to claim 2 for analysis of human respiration air, wherein the measuring head is a mouthpiece with a built-in volume transducer, said mouthpiece capable of allowing airflow in two directions, for the inspiration and expiration of air.

* * * * *